United States Patent
Berson et al.

(10) Patent No.: US 7,522,949 B2
(45) Date of Patent: *Apr. 21, 2009

(54) SENSOR WITH SIGNATURE OF DATA RELATING TO SENSOR

(75) Inventors: Thomas A. Berson, Palo Alto, CA (US); Bryan Olson, Sunnyvale, CA (US); Michael E. Fein, Mountain View, CA (US); Paul D. Mannheimer, Danville, CA (US); Charles E. Porges, Orinda, CA (US); David Schloemer, Stilwell, KS (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 10/776,444

(22) Filed: Feb. 10, 2004

(65) Prior Publication Data

US 2004/0162472 A1    Aug. 19, 2004

Related U.S. Application Data

(63) Continuation of application No. 09/662,246, filed on Sep. 14, 2000, now Pat. No. 6,708,049.

(60) Provisional application No. 60/156,488, filed on Sep. 28, 1999.

(51) Int. Cl.
*A61B 5/1455* (2006.01)

(52) U.S. Cl. .................................... 600/323; 600/331

(58) Field of Classification Search ......... 600/322–324, 600/331
See application file for complete search history.

(56) References Cited

U.S. PATENT DOCUMENTS

| | | | |
|---|---|---|---|
| 4,700,708 A | 10/1987 | New, Jr. et al. | |
| 4,816,824 A | 3/1989 | Katz et al. | |
| 4,942,877 A * | 7/1990 | Sakai et al. | 600/323 |
| 5,023,923 A | 6/1991 | Sanner et al. | |
| 5,208,858 A | 5/1993 | Vollert et al. | |
| 5,485,847 A | 1/1996 | Baker, Jr. | |
| 5,572,590 A | 11/1996 | Chess | |

(Continued)

FOREIGN PATENT DOCUMENTS

EP    0 949 506 A2    10/1999

(Continued)

OTHER PUBLICATIONS

"*Digital Certificates*", Warwick Ford, Scientific American, Oct. 1998, pp. 108.

(Continued)

*Primary Examiner*—Eric F Winakur
(74) *Attorney, Agent, or Firm*—Fletcher Yoder (57) ABSTRACT

A sensor has codes useful for a monitor which can be authenticated as accurate. The sensor produces a signal corresponding to a measured physiological characteristic and provides codes which can be assured of being accurate and authentic when used by a monitor. A memory associated with the sensor stores both data relating to the sensor and a digital signature. The digital signature authenticates the quality of the code by ensuring it was generated by an entity having predetermined quality controls, and ensures the code is accurate.

20 Claims, 10 Drawing Sheets

U.S. PATENT DOCUMENTS

| | | | |
|---|---|---|---|
| 5,638,447 A | 6/1997 | Micali | |
| 5,646,994 A | 7/1997 | Hill | |
| 5,646,997 A | 7/1997 | Barton | |
| 5,660,567 A | 8/1997 | Nierlich et al. | |
| 5,710,817 A | 1/1998 | Sjööquist | |
| 5,713,668 A | 2/1998 | Lunghofer et al. | |
| 5,720,293 A * | 2/1998 | Quinn et al. | 600/505 |
| 5,737,419 A | 4/1998 | Ganesan | |
| 5,748,735 A | 5/1998 | Ganesan | |
| 5,761,305 A | 6/1998 | Vanstone et al. | |
| 5,768,389 A | 6/1998 | Ishii | |
| 5,779,630 A | 7/1998 | Fein et al. | |
| 5,787,178 A | 7/1998 | Schwenk | |
| 5,790,675 A | 8/1998 | Patarin | |
| 5,817,009 A | 10/1998 | Rosenheimer et al. | |
| 5,842,977 A * | 12/1998 | Lesho et al. | 600/300 |
| 5,850,443 A | 12/1998 | Van Oorschot et al. | |
| 5,860,099 A | 1/1999 | Milios et al. | |
| 5,867,577 A | 2/1999 | Patarin | |
| 5,987,343 A | 11/1999 | Kinast | |
| 5,995,855 A | 11/1999 | Kiani et al. | |
| 6,026,293 A * | 2/2000 | Osborn | 455/411 |
| 6,126,613 A * | 10/2000 | Edwards et al. | 600/359 |
| 6,170,058 B1 * | 1/2001 | Kausik | 713/193 |
| 6,266,551 B1 | 7/2001 | Osadchy et al. | |
| 6,298,255 B1 | 10/2001 | Cordero et al. | |
| 6,307,938 B1 | 10/2001 | Matyas, Jr. et al. | |
| 6,308,089 B1 * | 10/2001 | von der Ruhr et al. | 600/338 |
| 6,584,336 B1 * | 6/2003 | Ali et al. | 600/323 |
| 6,708,049 B1 * | 3/2004 | Berson et al. | 600/323 |

FOREIGN PATENT DOCUMENTS

| | | | |
|---|---|---|---|
| WO | WO 97/29678 | * | 8/1997 |

OTHER PUBLICATIONS

"*Cryptography for the Internet*", Philip R. Zimmermann, Scientific American, Oct. 1998, pp. 111-115.

"*The Case against Regulating Encryption Technology*", Ronald L. Rivest, Scientific American, Oct. 1998, pp. 116-117.

"*Handbook of Applied Cryptography*", Alfred J. Menezes et al., Library of Congress, CRC Press 1997, pp. 438-444.

"*Information technology—Security techniques —Digital signature schemes giving message recovery*", International Standard, ISO/IEC 9796-2: 1997(E).

Chapter 8—Public-Key Encryption.

\* cited by examiner

SENSOR WITH SIGNATURE OF DATA RELATING TO SENSOR

CROSS-REFERENCE TO RELATED APPLICATIONS

This application is a continuation of U.S. application Ser. No. 09/662,246, filed Sep. 14, 2000, now U.S. Pat. No. 6,708, 049, issued Mar. 16, 2004, which claims the benefit of U.S. Provisional Application No. 60/156,488, filed Sep. 28, 1999, the disclosures of which are incorporated by reference.

BACKGROUND OF THE INVENTION

The present invention relates to sensors having a memory. It will be described in particular with respect to pulse oximeter sensors, but is equally applicable to other types of sensors as well.

Pulse Oximetry

Pulse oximetry is typically used to measure various blood flow characteristics including, but not limited to, the blood-oxygen saturation of hemoglobin in arterial blood, and the rate of blood pulsations corresponding to a heart rate of a patient. Measurement of these characteristics has been accomplished by use of a non-invasive sensor which passes light through a portion of the patient's tissue where blood perfuses the tissue, and photoelectrically senses the absorption of light in such tissue. A monitor, connected to the sensor, determines the amount of light absorbed and calculates the amount of blood constituent being measured, for example, arterial oxygen saturation.

The light passed through the tissue is selected to be of one or more wavelengths that are absorbed by the blood in an amount representative of the amount of the blood constituent present in the blood. The amount of transmitted or reflected light passed through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Various methods have been proposed in the past for coding information in sensors, including pulse oximeter sensors, to convey useful information to a monitor. For example, an encoding mechanism is shown in Nellcor U.S. Pat. No. 4,700, 708, the disclosure of which is hereby incorporated by reference. This mechanism relates to an optical oximeter probe which uses a pair of light emitting diodes (LEDs) to direct light through blood-perfused tissue, with a detector detecting light which has not been absorbed by the tissue. Oxygen saturation calculation accuracy depends upon knowing the wavelengths of the LEDs. Since the wavelengths of LEDs can vary, a coding resistor is placed in the probe with the value of the resistor indicating to the monitor the oximeter oxygen saturation calculation coefficients appropriate for the actual wavelengths of at least one of the LEDs or the LED wavelength combination for the sensor. When the oximeter instrument is turned on, it first applies a current to the coding resistor and measures the voltage to determine the value of the resistor and thus appropriate saturation calculation coefficients to use for the wavelengths of the LEDs in the probe.

Other coding mechanisms have also been proposed in U.S. Pat. Nos. 5,259,381; 4,942,877; 4,446,715; 3,790,910; 4,303, 984; 4,621,643; 5,246,003; 3,720,177; 4,684,245; 5,645,059; 5,058,588; 4,858,615; and 4,942,877, the disclosures of which are all hereby incorporated by reference. The '877 patent in particular discloses storing a variety of data in a pulse oximetry sensor memory, including coefficients for a saturation equation for oximetry.

A problem with prior art sensor coding techniques is that information encoding may sometimes be inaccurate and/or not authentic. This results in the monitor sometimes not being able to obtain adequate readings from a patient, or worse yet making inaccurate calculations, such that in extreme instances the inaccurate codes and resulting inadequate readings might significantly impair patient safety and contribute to bad patient outcomes. Inaccurate codes can result under a variety of circumstances. For example, errors can occur during a manufacturing process or during shipment of the sensor. More common, however, is that inaccurate codes are somewhat purposely used by discount low quality third party sensor manufacturers who are not licensed or authorized by the corresponding monitor manufacturer to supply compatible high quality sensors. These third parties often invest minimal amounts in research and simply do not understand what the codes are for since they do not understand how the monitor works or how the monitor uses the codes. Since they are not licensed by the monitor manufacturer, this information is generally not available from the monitor manufacturer. All too often, these third parties choose not to invest time and expense to learn by reverse engineering techniques or original science how the monitors work and how the codes are used to ensure patient safety. Rather, numerous instances exist where such third parties simply examine a range of code values used in the market for each data characteristic being encoded, and take an average code value for all their sensors so as to be "compatible" with a particular monitor. Though in many instances using an average code value will simply result in readings being out of specification but not otherwise particularly dangerous, the average code value may be sufficiently wrong to introduce significant errors into the computation algorithms used by the monitor and to cause significant patient safety problems. In addition, whenever third party inaccurate codes contribute to a bad patient outcome, the harmed patient, or his or her heirs, can attempt to hold the monitor manufacturer, together with the direct caregivers, responsible. If the caregivers have not retained the low quality third party sensor used and made no record of its use, which happens, it would be difficult for the monitor manufacturer to establish that the problem was caused by use of the low quality third party sensor with its otherwise high quality monitor.

Another reason that there is a need for authentication of digital data stored in association with medical sensors is the small but real possibility that data will be corrupted between the time of recording in the factory and the time of reading by the instrument which is monitoring the condition of a patient. One often-cited example of a mechanism which may cause such corruption is the changing of a value recorded in digital memory by the incidence of an energetic cosmic ray. A more ordinary source of corruption is damage to a memory cell caused by electrostatic discharge.

Accordingly, a need exists in the art to devise a way to communicate accurate and authentic complex codes from a sensor to a monitor to ensure accurate computations and accurate patient monitoring by the monitor.

SUMMARY OF THE INVENTION

Accordingly, it is an object of the invention to provide a sensor which has codes useful for a monitor which can be authenticated as accurate.

This and other objects are achieved by a sensor which produces a signal corresponding to a measured physiological characteristic of a patient and which provides codes which can be assured of being accurate and authentic when used by a monitor. A memory associated with the sensor stores the codes and other data relating to the sensor, the memory also containing a digital signature. The digital signature authenticates the quality of the codes and data by ensuring it was generated by an entity having predetermined quality controls, and ensures the codes are accurate.

In one embodiment, the digital signature is produced during the sensor manufacturing process using a private key of a private key and public key pair, with the signature then being verifiable with the public key embedded in processors in an external sensor reader (e.g., monitor). The signature can be separate from the data. Or, instead of the signature being appended to the data, the signature itself can contain all or at least some of the data and thus provides a level of masking of the data.

According to one embodiment of the invention, any one of several known public/private key signature methods can be used. These include Diffie-Hellman (and its variants, such as the Digital Signature Standard from the National Institute of Standards and Technology, El Gamal and the elliptic curve approaches), RSA (developed at the Massachusetts Institute of Technology), and Rabin-Williams.

In a further embodiment of the invention, a digest of a portion of the data to be signed is included in the signature to verify that errors in the data have not occurred. Each piece of data preferably is organized to include a field ID, indicating the type of data to follow, followed by a data length element, followed by the piece of data. A mandatory bit is also preferably provided indicating whether knowledge of how to use the piece of data by the monitor is mandatory for operation of the sensor with the monitor. Thus, an older monitor which does not recognize a non-critical piece of data can simply disregard it, since presumably it will not implement the enhanced feature which corresponds to the piece of data. However, if the piece of data is necessary for proper operation of a sensor, the mandatory bit will be set, and the sensor reader/monitor will indicate that it cannot use the particular sensor that has been plugged in.

In yet another embodiment, the signed data stored with the sensor would include at least a sensor dependent saturation calibration curve coefficient used to calculate oxygen saturation by a monitor. Additionally, the data may include sensor OFF thresholds and thermistor calibration coefficients appropriate for sensors including a thermistor. Some of such data may be included within the signature, and this or other data could be included outside the signature. The data outside the signature could be encrypted (or masked), if desired, with a symmetric key cryptographic algorithm, for example the Data Encryption Standard (DES) from NIST, and the symmetric key could be included in the signature. Alternatively, the symmetric key could be derivable from the digest, which is contained within the signature.

For a further understanding of the nature and advantages of the invention, reference should be made to the following description taken in conjunction with the accompanying drawings.

DESCRIPTION OF THE SPECIFIC EMBODIMENTS

Definitions

SIGNED DATA is data which has been included in the computation of a digest (by use of a hash function), this digest being in turn included in the computation of a digital signature, so that any later alteration of the data will be detectable by a failure of verification of the digital signature. Data which have been signed may eventually reside either inside or outside the digital signature. In the process known as "digital signature with message recovery," the data reside entirely within the digital signature. Until the signature is verified, the data are in a scrambled form, so that the casual observer cannot understand them. The mathematical process that verifies the signature unscrambles, or "recovers" the data. In the process known as "digital signature with partial recovery," which is preferred for the invention described herein, a portion of the signed data is included within the signature, and additional data reside outside the signature. The data portion within the signature is obscured until the signature is verified, but the portion outside remains easily readable, unless a masking process is used to obscure it.

MASKED DATA, as the term is used herein, are data which have been encrypted so as to be recoverable with an unmasking key which is included within the signature. During verification of the signature, the unmasking key is recovered. That unmasking key may then be used to decrypt the masked data. In a preferred embodiment, the masked data are encrypted under a symmetric key, which is to say that the encryption and decryption keys (i.e. the masking and unmasking keys) are identical. In an especially preferred embodiment, the message digest that is incorporated in the digital signature is used as a symmetric key for masking and unmasking data outside the signature.

Sensor Reader/Monitor

Figure 1:
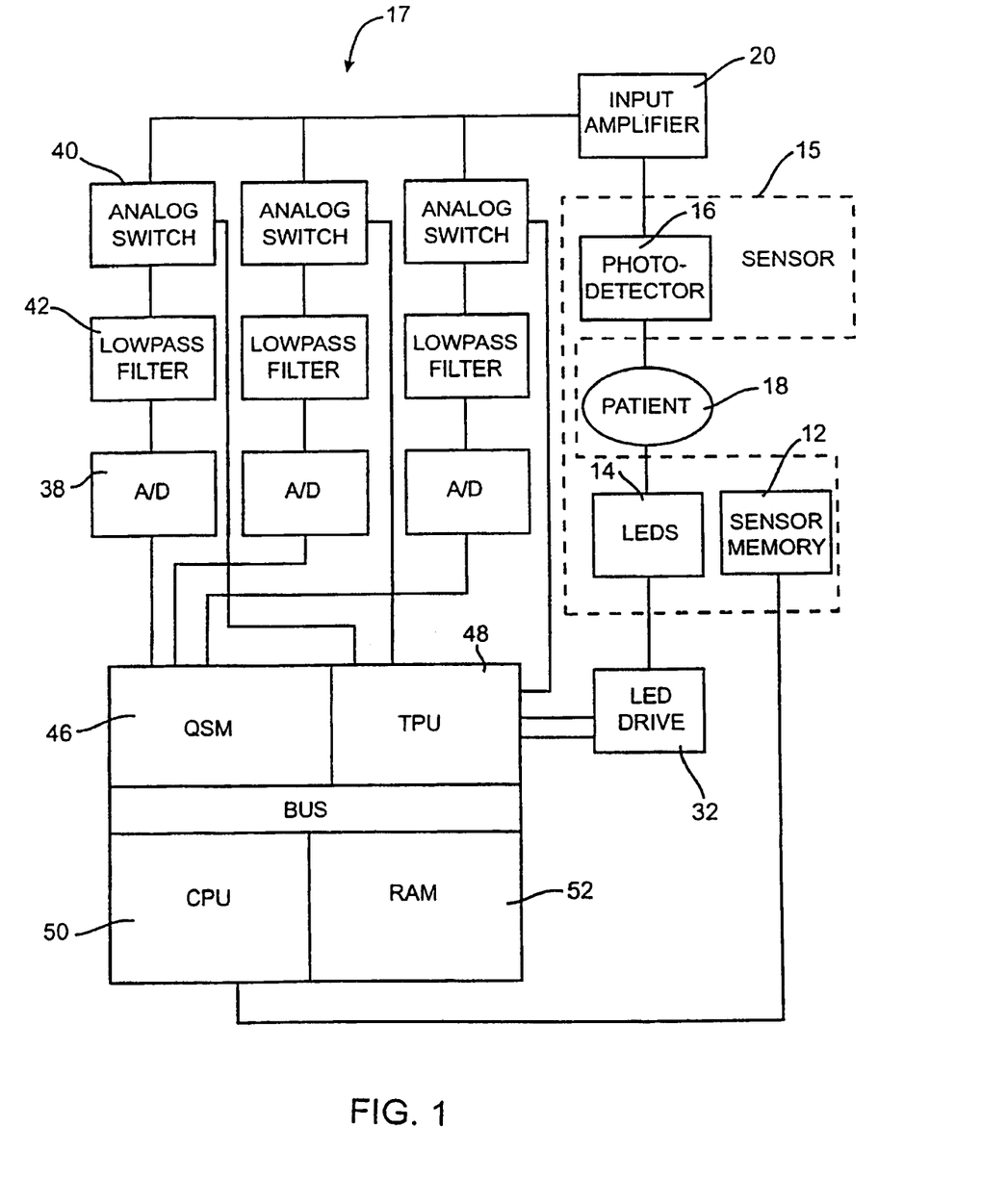
FIG. 1 is a block diagram of a sensor and sensor reader system incorporating the invention.

FIG. 1 is a block diagram of one preferred embodiment of the invention. FIG. 1 shows a pulse oximeter 17 (or sensor reader) which is connected to a non-invasive sensor 15 attached to patient tissue 18. Light from sensor LEDs 14 passes into the patient tissue 18, and after being transmitted through or reflected from tissue 18, the light is received by photosensor 16. Two or more LEDs can be used depending upon the embodiment of the present invention. Photosensor 16 converts the received energy into an electrical signal, which is then fed to input amplifier 20.

Light sources other than LEDs can be used. For example, lasers could be used, or a white light source could be used with appropriate wavelength filters either at the transmitting or receiving ends.

Time Processing Unit (TPU) 48 sends control signals to the LED drive 32, to activate the LEDs, typically in alternation. Again, depending on the embodiment, the drive may control two or any additional desired number of LEDs.

Figure 3:
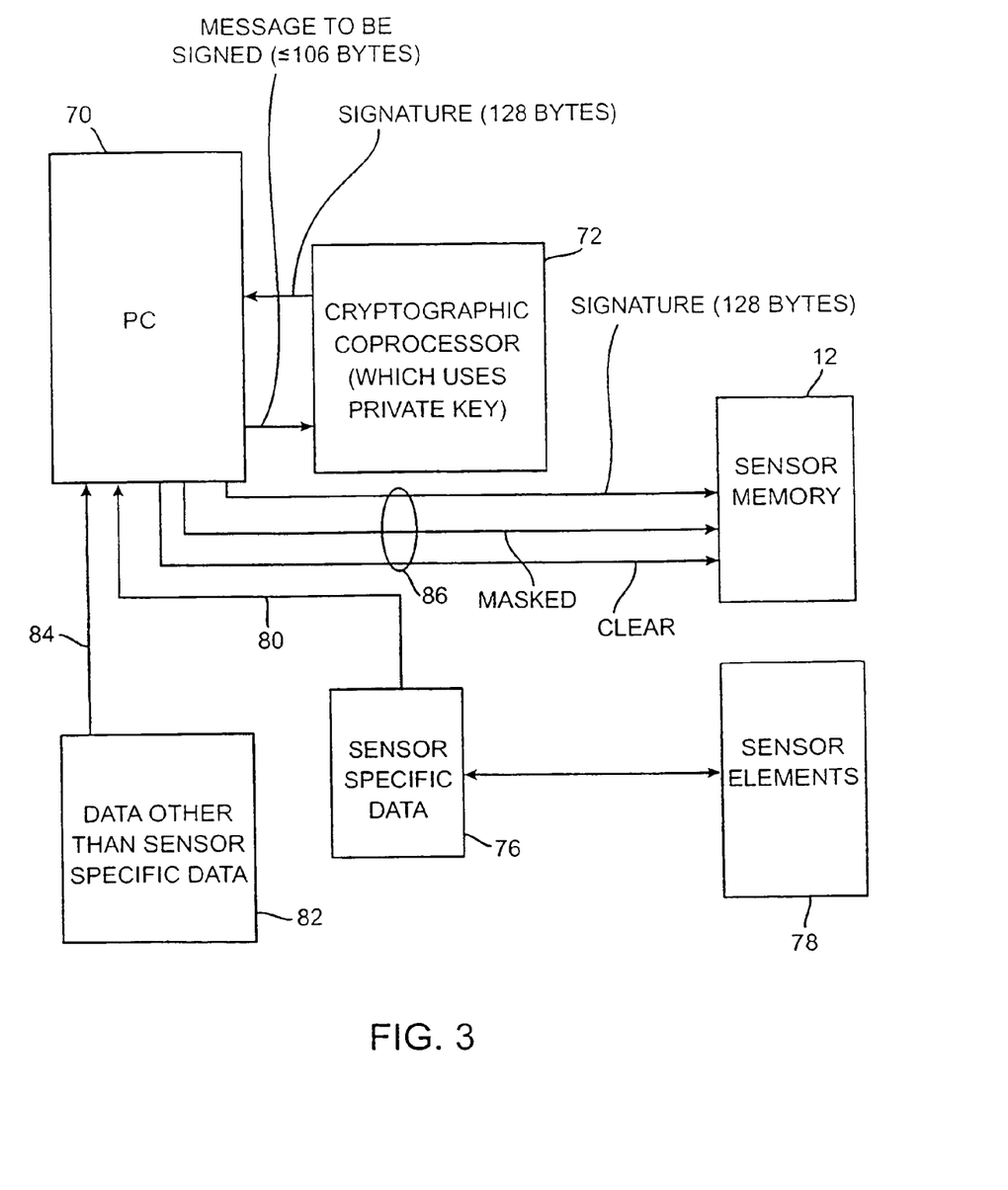
FIG. 3 is a block diagram illustrating a system for signing data during the manufacture of a sensor.

The signal received from input amplifier 20 is passed through three different channels as shown in the embodiment of FIG. 3 for three different wavelengths. Alternately, two channels for two wavelengths could be used, or N channels for N wavelengths. Each channel includes an analog switch 40, a low pass filter 42, and an analog to digital (A/D) converter 38. Control lines from TPU 48 select the appropriate channel at the time the corresponding LED 14 is being driven, in synchronization. A queued serial module (QSM) 46 receives the digital data from each of the channels via data lines from the A/D converters. CPU 50 transfers the data from QSM 46 into RAM 52 as QSM 46 periodically fills up. In one embodiment, QSM 46, TPU 48, CPU 50 and RAM 52 are part of one integrated circuit, such as a microcontroller.

Sensor Memory

Sensor 15, which includes photodetector 16 and LEDs 14, has a sensor memory 12 associated with it. Memory 12 is connected to CPU 50 in the sensor reader or monitor 17. The memory 12 could be packaged in a body of the sensor 15 or in an electrical plug connected to the sensor. Alternatively, the memory 12 could be packaged in a housing which is attachable to an external surface of the monitor, or the memory 12 could be located anywhere in a signal path between the sensor body and the monitor. Specifically, according to some preferred embodiments, a content of the sensor memory 12 could be constant for all sensors associated with a particular sensor model. In this case, instead of putting an individual memory 12 on each sensor associated with this model, the memory 12 could instead be included in a reusable extension cable associated with the sensor model. If the sensor model is a disposable sensor, in this case a single memory 12 could be incorporated into a reusable extension cable. The reusable cable could then be used with multiple disposable sensors.

Figure 2:
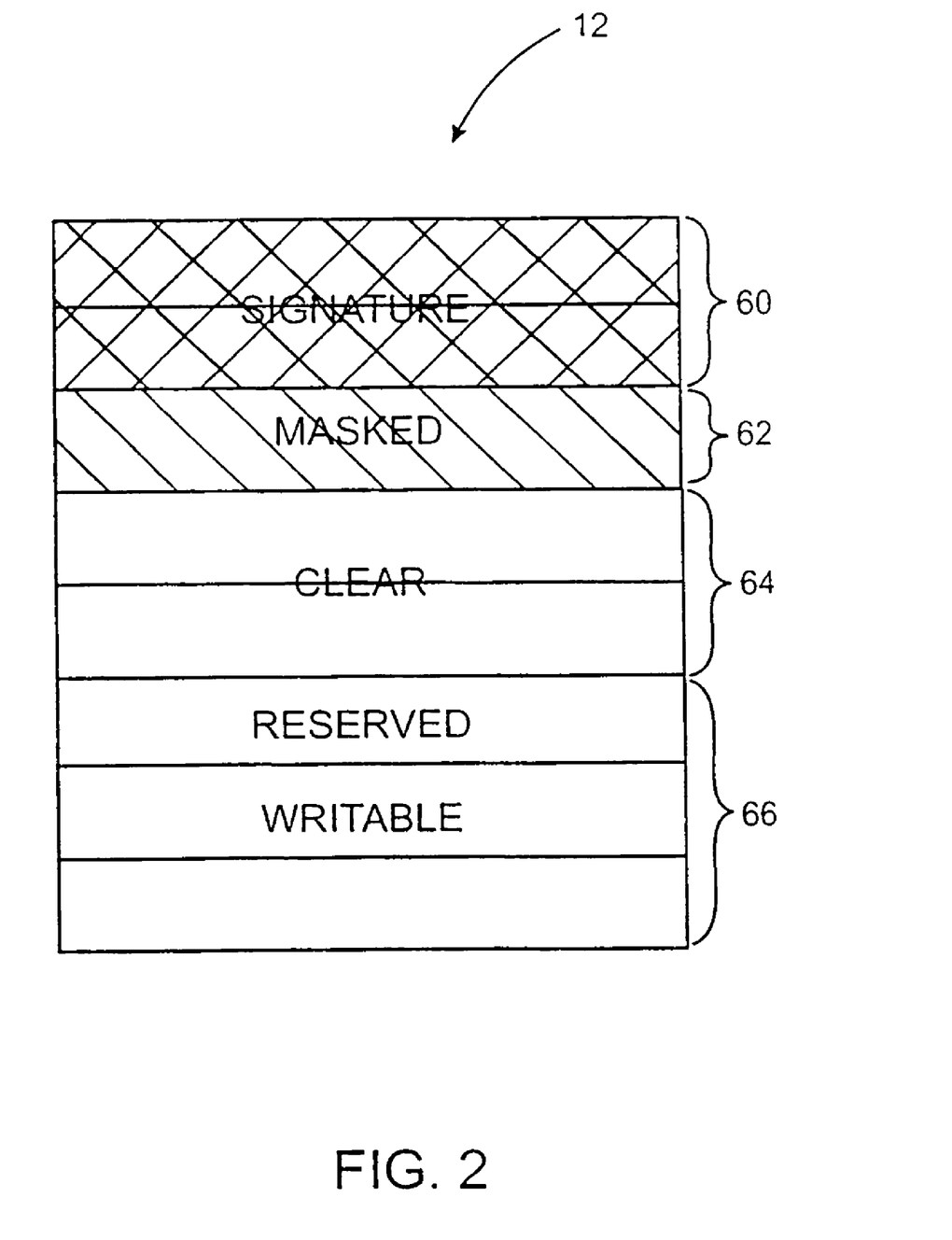
FIG. 2 is a block diagram of the contents of a sensor memory shown in FIG. 1.

FIG. 2 is a diagram of the contents of memory 12 of FIG. 1 according to one preferred embodiment. A digital signature 60 occupies a first portion of the memory, with the signature preferably including sensor related data. A second portion 62 contains data which are signed and masked. A third portion 64 includes data which are signed but remain clear (i.e., they are not masked). Finally, a portion 66 is reserved for writing to the sensor memory by the sensor reader. Portion 66 is neither signed nor masked. While this preferred embodiment is shown for illustrative purposes, it should be understood that memory 12 may contain many different blocks of data outside the digital signature, each of which may be signed and/or masked according to the requirements of a particular embodiment. These different blocks of data may be arranged in any desired order, e.g., multiple signed and unsigned blocks may be interleaved, and multiple masked and unmasked blocks may be interleaved. It should also be understood that data written to memory 12 by the sensor reader is an optional feature, and that such data may optionally be masked.

Writing of Signature at Factory

FIG. 3 is a block diagram of one embodiment of a system used in a factory to write a signature into the sensor memory 12. Shown in FIG. 3 is a personal computer 70 and an associated cryptographic coprocessor 72 which contains and utilizes a private key of a private/public key pair. The private key is contained within a memory within coprocessor 72. This key is preferably not readable by anyone to preserve security. The corresponding public key may be known by both the PC 70 and coprocessor 72, or may be outputted by the coprocessor 72.

The data which are signed by the coprocessor 72 can come from more than one source. Shown is a tester 76 for testing the sensor to determine the value of certain sensor components 78, such as LED wavelength, thermistor resistance, etc. These data values are then provided to PC 70 along line 80. Additional information 82 may be input by a keyboard or from another database along lines 84. This data may include, for example, a serial number for the sensor, a manufacturing date, a lot number, a digest of the portion of the data to be signed, or other information.

The data to be signed and other data to be included in the memory 12 are passed from the PC to cryptographic coprocessor 72. The coprocessor 72 computes a digest from the data being signed, and signs, with the private key, the digest and other data whose signing is desired. The signature and data contained therein can include a symmetric key for other data being masked, or information from which a symmetric key can be derived. The coprocessor transmits the signature back to PC 70. PC 70 preferably masks some of the data which are not included in the signature, and combines the masked data, signature, and clear data and transmits all this to memory 12 on lines 86.

Figure 4:
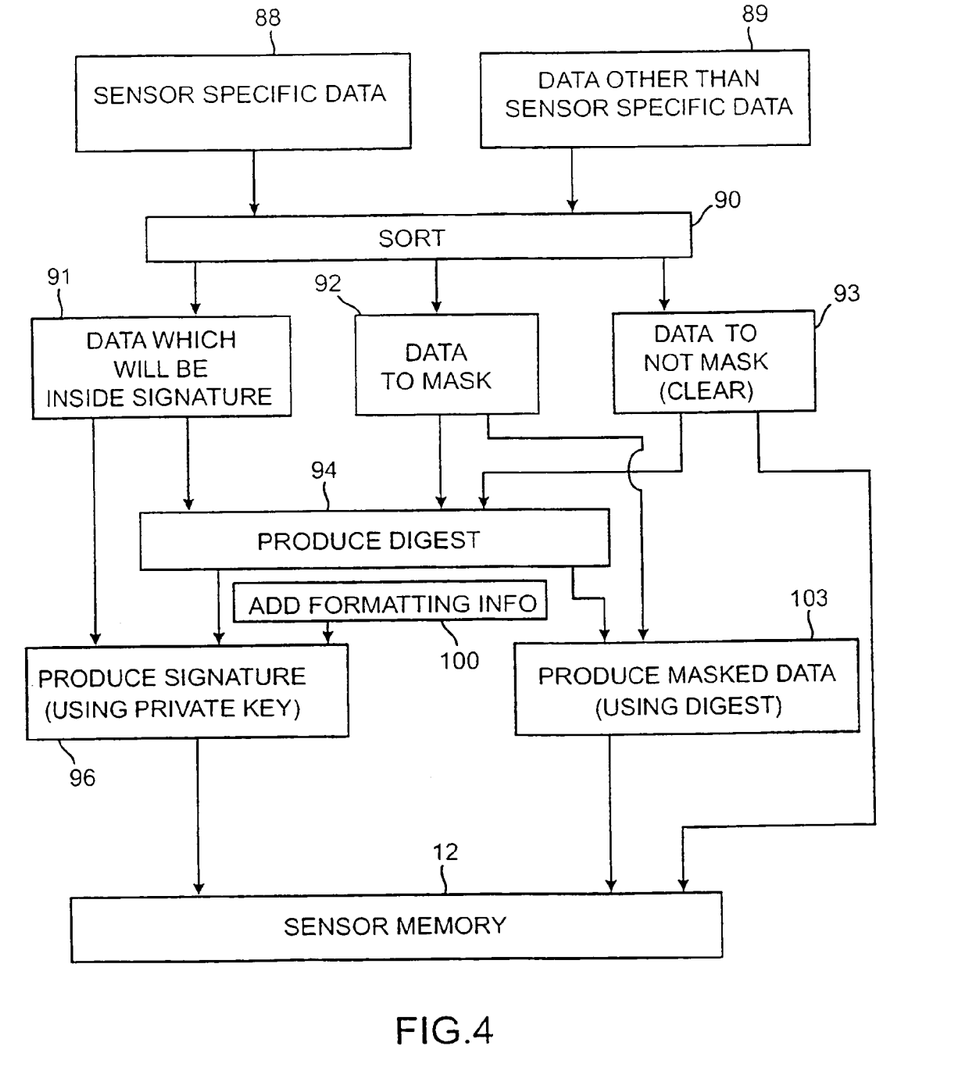
FIG. 4 is a diagram illustrating the signing mechanism by the system of FIG. 3.
Figure 5:
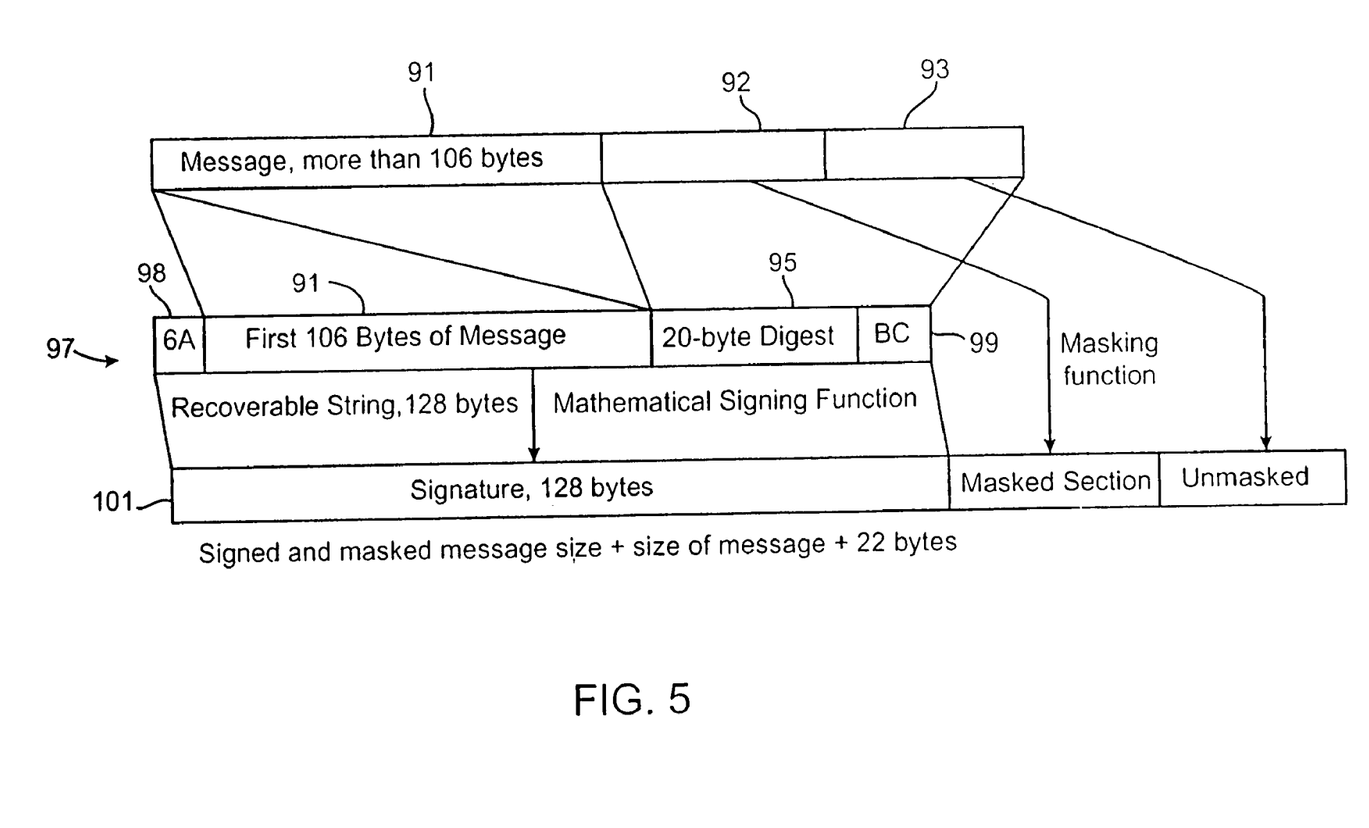
FIG. 5 is a data flow diagram illustrating the data generated in the method of FIG. 4.

FIG. 4 is a diagram illustrating the operation of the system of FIG. 3. FIG. 5 illustrates the data flow according to the method of FIG. 4.

First, the sensor is tested and measured parameters 88 of the sensor, such as LED wavelength, are provided. Next, any other data 89 is input. The data is then sorted (step 90). This sort results in first data 91 to be signed, second data 92 to be masked, and third data 93, which will be in the clear, i.e., neither masked nor signed. To verify no errors occur in any of the data 91, 92, 93 during manufacture or during a subsequent reading/decryption step when the sensor is used, a digest 95 is created (step 94) from all the data 91, 92, 93 during manufacture and is included within the signature. The digest is produced as an output of a hash function applied to the data 91, 92, 93. The digest can be compared to a complicated CRC. When the data and the digest are later read by a monitor subsequent to decryption, if one or more bits of error occurred in any of the data 91, 92, 93, a second digest the monitor will create from the read data will not correspond to the digest extracted from the memory, thus indicating one or more errors have been introduced somewhere in the writing or signature verification processes. An example of a suitable hash function is SHA-1, described in Federal Information Processing Standard Publication FIPS, PUB 180-1, *Secure Hash Standard*, National Institute of Standards & Technology, 1995. The digest 95 and data 91 are signed along with formatting data 99 added in step 100 to produce a signature 101 in step 96. The formatting data is added in step 100, for example in accordance with International Standard ISO/IEC 9796-2, a standard for digital signatures. The data 92 is masked in step 103. This signature 101, masked data 103, and clear data 93 are then combined by the coprocessor 72 and PC 70 and stored in sensor memory 12.

The private key used to sign the data 91 is preferably a Rabin-Williams digital signature algorithm, one example of which is described in ISO 9796-2.

In one embodiment, the original block of data to be signed, block 91, is 73 bytes or less plus a 20 byte digest plus 3 bytes of formatting data 99. This yields a signed message of 96 bytes. Longer signatures can be used as well, e.g., signatures having 128 bytes with 106 bytes being receivable as useful data 91. The length of the signature depends on the degree of security desired and the amount of decryption ability of the monitor.

Reading Signature by Reader/Monitor in Field

Figure 6:
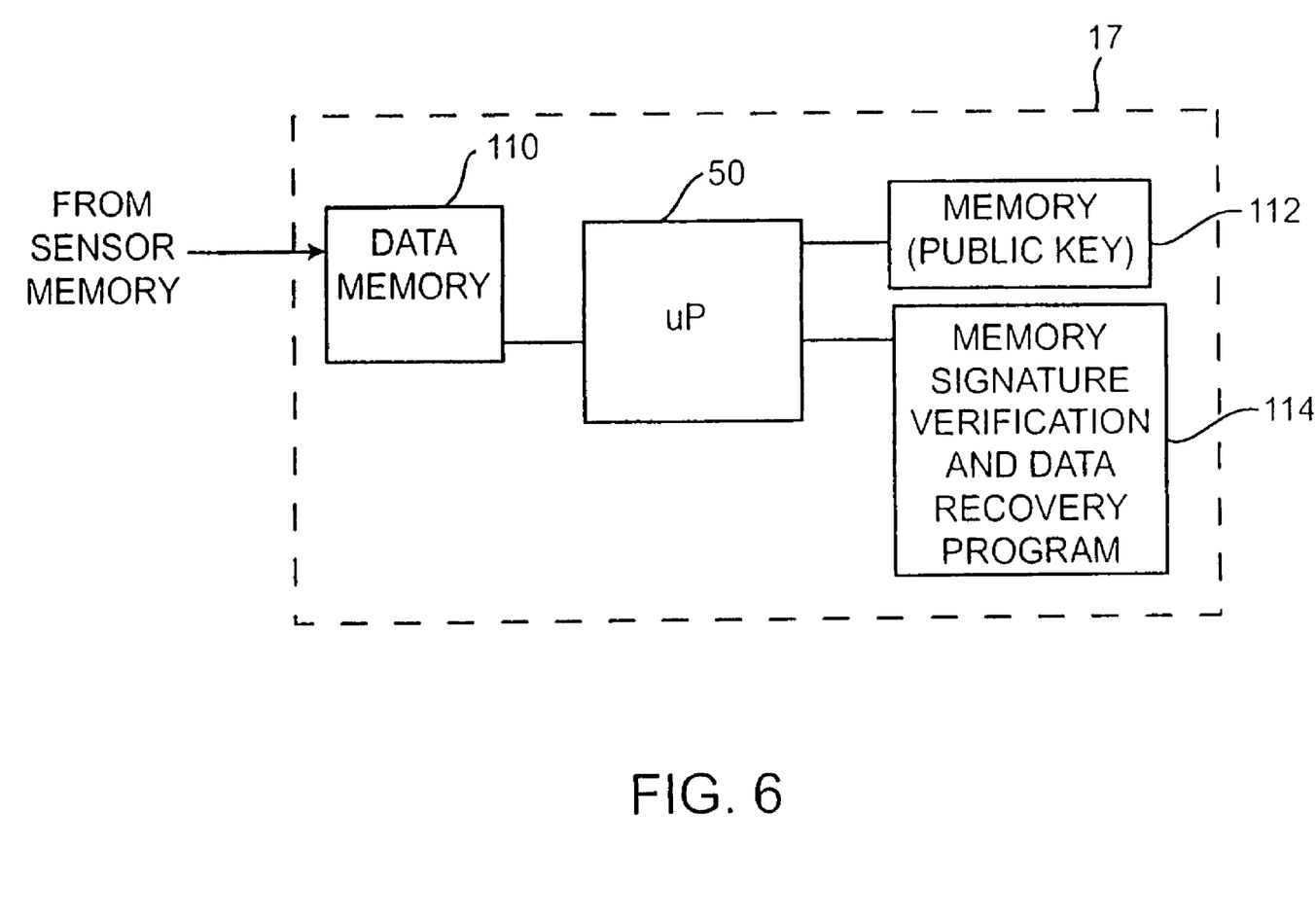
FIG. 6 is a diagram of one embodiment of a sensor reader or monitor, illustrating different software modules.

FIG. 6 illustrates a portion of a sensor reader or monitor 17 for verifying the digital signature and recovering the data from a sensor when used on a patient. The data are first retrieved from the sensor memory and stored in a memory 110 by CPU 50. The sensor reader has a public key in a memory 112, which is typically loaded at the time of manufacture of the monitor or is provided as an upgrade of the monitor. A signature verification and data recovery program is stored in a portion of memory 114.

Figure 7:
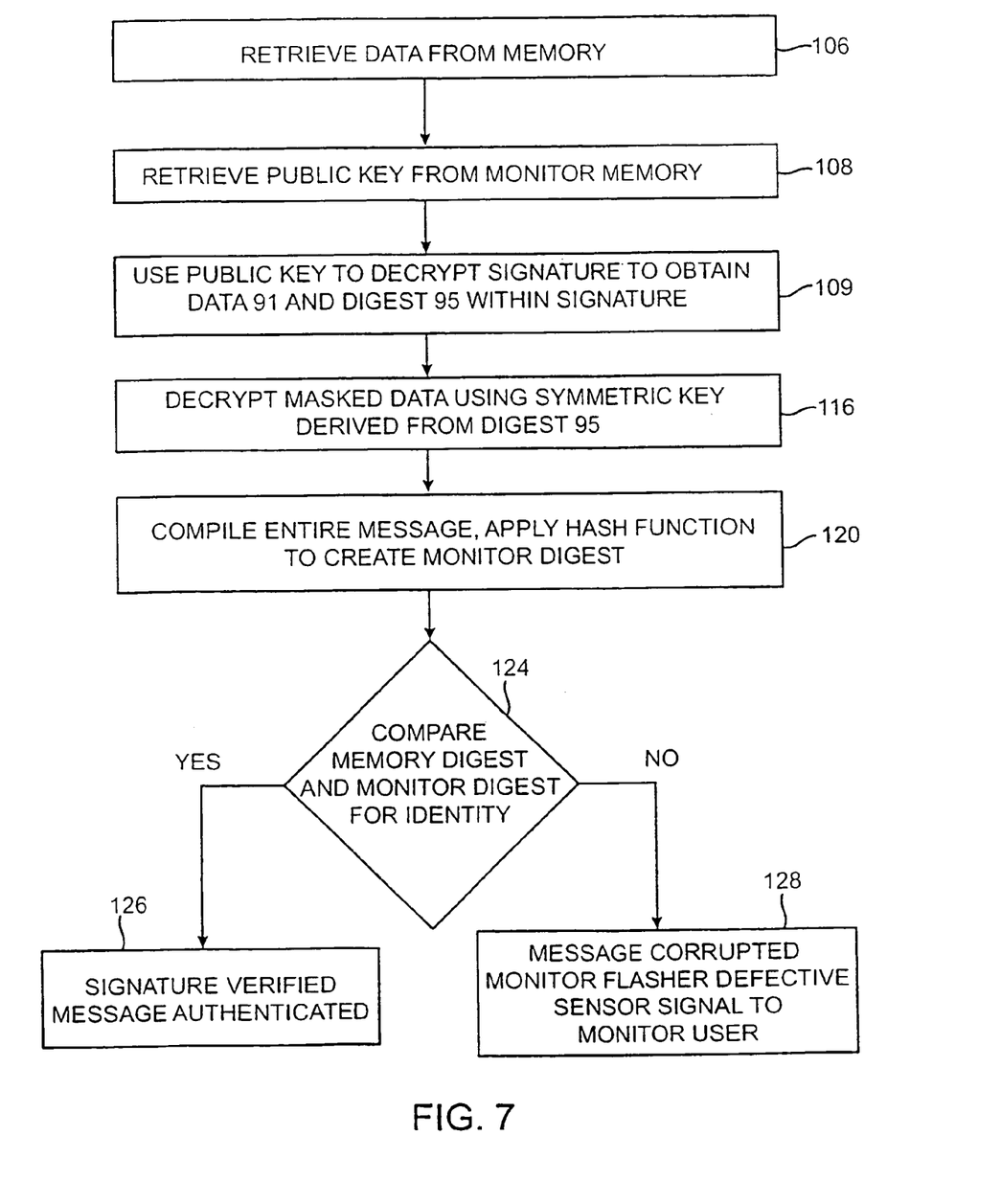
FIG. 7 is a flowchart illustrating the reading of a sensor according to the invention.
Figure 8:
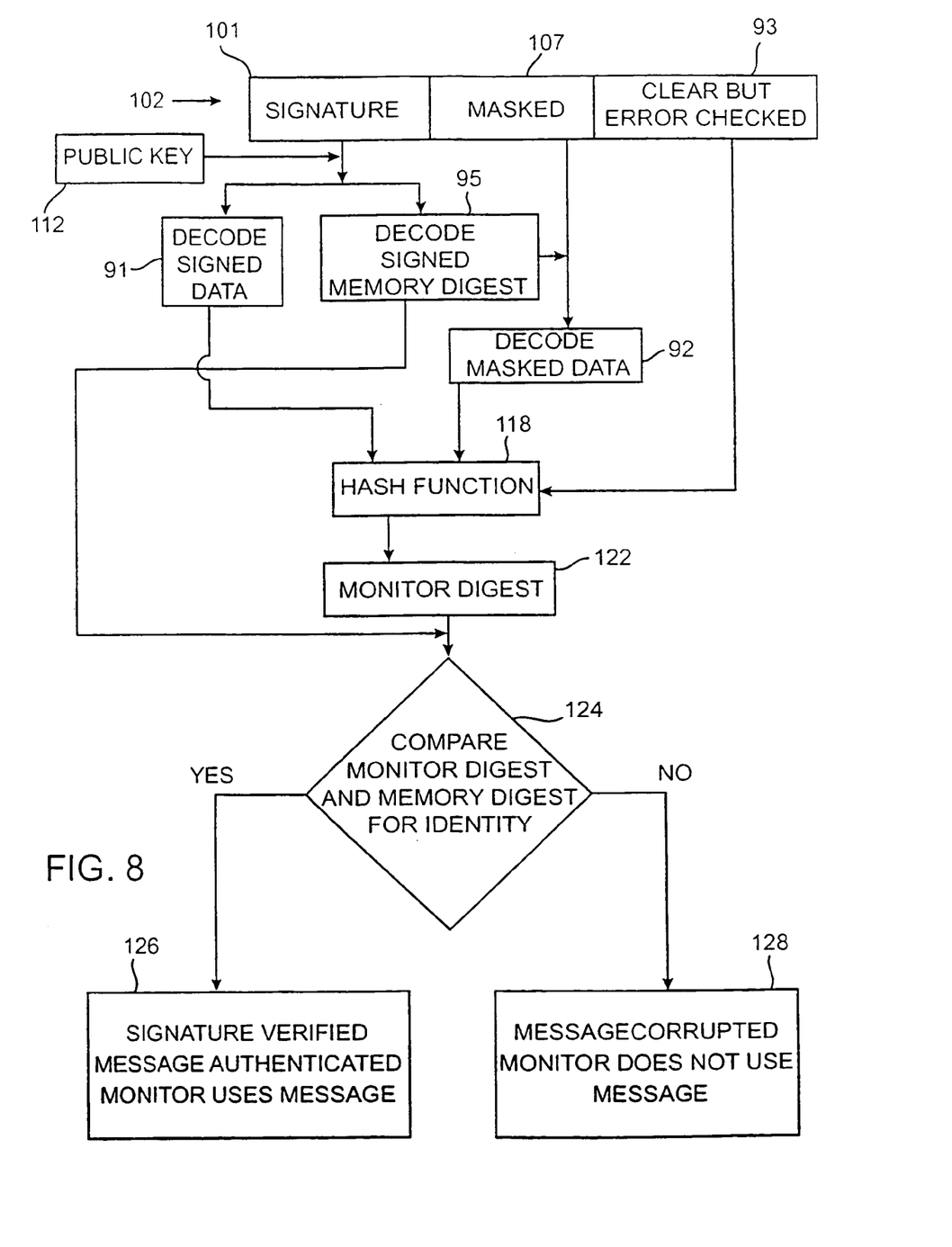
FIG. 8 is a diagram illustrating the flow of data read in the method of FIG. 7.

FIG. 7 illustrates the operation of the signature verification and data recovery program of memory portion 114 of FIG. 6. FIG. 8 is a diagram illustrating the movement of the data according to the flowchart of FIG. 7. Data is first retrieved from the sensor memory in step 106. The data 102 retrieved is shown in FIG. 8 as consisting of signature 101, the masked data 107 and the clear data 93. The public key 112 is then retrieved from the monitor's memory (step 108).

The signature and public key are then provided as inputs to a cryptographic transform to obtain the signature data 91 and the memory digest 95 (step 109).

The memory digest is used to determine the masked data symmetric key, and this key is then used to decrypt the masked data 107 to obtain the original data 92 that was masked (step 116).

In order to verify the accuracy of all the data 91, 92, 93, a second digest is then created by the monitor from the decrypted signed data 91, the unmasked data 92, and the clear data 93 using a hash function 118 (step 120). This will create a new digest 122 which then can be compared with the original digest 95 (read from the memory) in a step 124. If the digests are the same, the signature is verified and the message (combined data 91, 92, 93) is authenticated (step 126). The monitor then uses the message in its operation. If, on the other hand, the digests are not the same, the message is determined to be corrupted and the monitor will indicate a defective sensor signal to the monitor user and not use the message (128).

As can be seen, the invention uniquely applies digital signatures to sensors and in particular pulse oximeter sensors. The unique application to a sensor allows the sensor reader/monitor to verify message (data) accuracy, authenticity as to source and quality of the sensor, and protects sensitive sensor specification information from being easily discovered and used erroneously by non-innovative sensor manufacturers.

Signature Fields

Figure 9:
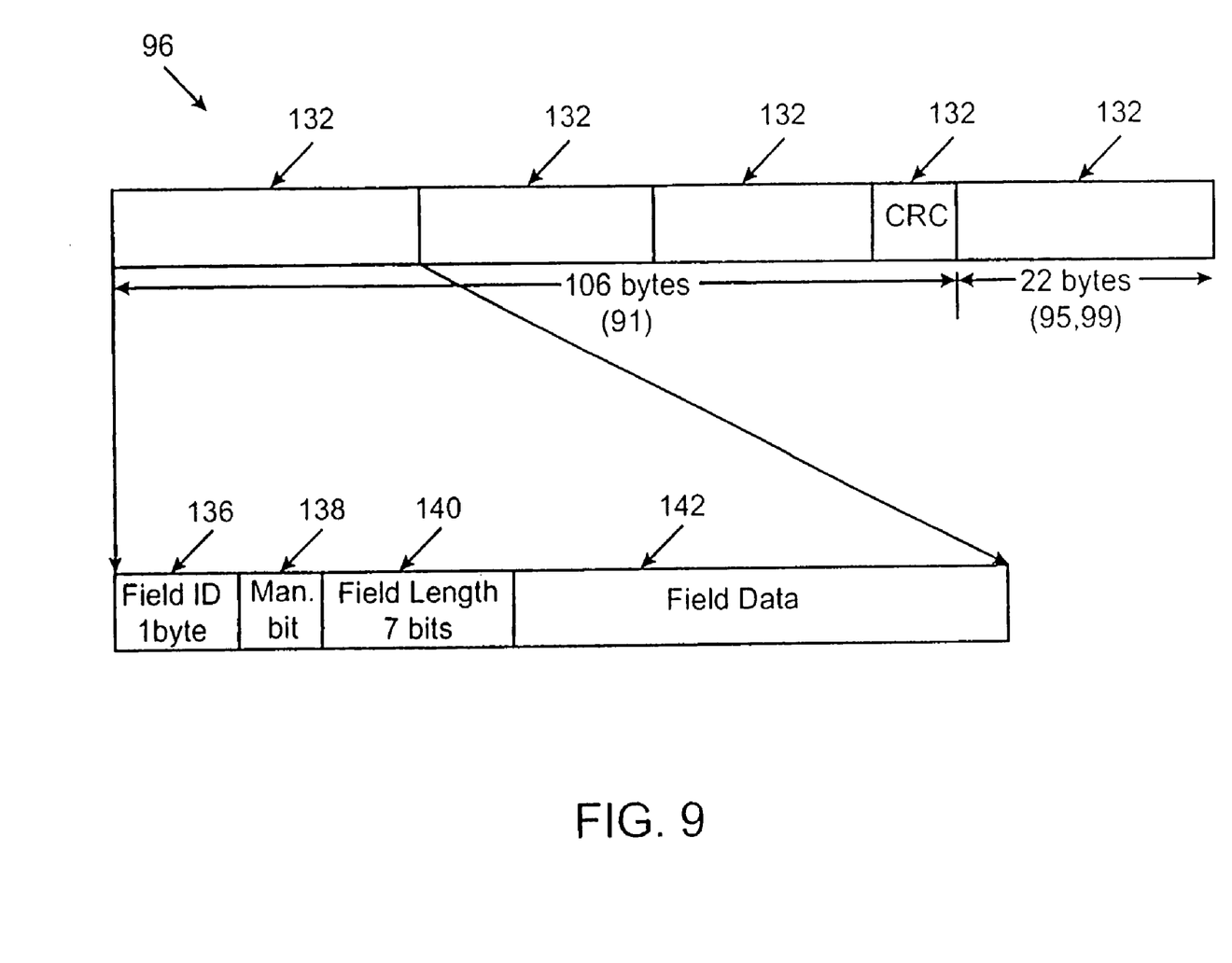
FIG. 9 is a diagram of different fields in the data.

FIG. 9 illustrates in more detail one embodiment of the signature data 91, digest 95, and formatting data 99. In particular, signature data 91 is broken up into an arbitrary number of fields 132, followed by a CRC 134. Each field 132 includes a 1 byte field ID 136, which identifies the type of data presented in its field. A single bit 138 indicates whether that field is mandatory or not. Next, there are 7 bits in a block 140 identifying the length of the field. Finally, the field data is provided in a byte block 142.

In operation, if an existing monitor or sensor reader is not able to handle or does not recognize the particular field ID 136, it can look to the field length 140 and figure out how much data to skip to get to the next field. However, it first checks mandatory bit 138 to determine whether this data is mandatory to operation of the sensor. If it is mandatory, the monitor or sensor reader will produce an error message indicating that it is unable to properly read the attached sensor. If it is not mandatory, the monitor or sensor reader will simply ignore this data field.

This field format thus provides flexibility in packing data into the signature data block, and also upgradeability and compatibility with existing sensor readers and future generations of sensors and monitors.

In one embodiment, a field identifier of a selected value is designated as an "escape character", indicating that the next character is the identifier of an extended set. This allows the ability to add, delete, move, compress or stretch the fields that are included in a message without having to resort to fixed addresses.

Data Types

The following are examples of data types that might be included in the memory 12 in one embodiment.

The actual coefficients or data to be applied to the equations for the saturation calculation for a pulse oximeter could be stored. These coefficients can be stored in lieu of storing a value corresponding to the measured LED wavelength. The result is greatly increased flexibility in sensor design, since calibration curves are not restricted to a small set of curves which have been provided in instruments.

Alternately to the coefficients or in addition thereto, the LED wavelengths could simply be stored. Also, secondary emission wavelength characteristics could be stored, and other LED parameters.

Certain sensors may have thermistors used to measure local temperature for purposes such as compensation of calibration curves for sensor temperature, or to prevent patient burns. Calibration coefficients for the thermistor could be stored.

Other data that might be included in memory 12 could include, for example, a lot code which will allow traceability of the sensor, a bad sensor flag, a date of manufacture, manufacturing test information, the version of the signing software program used for the signature, LED forward V/I characteristics, LED optical power characteristics, a detector efficiency characteristic, a maximum safe LED power, a sensor data set revision level (indicating the features included in the sensor), a sensor model ID, an adult/neonatal query flag (for triggering a desired alarm limit range depending upon whether a neonate or adult is monitored, with different normal oxygen saturation levels for pulse oximetry), a write once/write many flag, a page size, a number of pages, and a maximum number of recycle events.

Alternately, any of the data types mentioned above or described in the cited prior art references could be used and stored in either masked data 92, in the signature data 91, or in the clear data 93.

Figure 10:
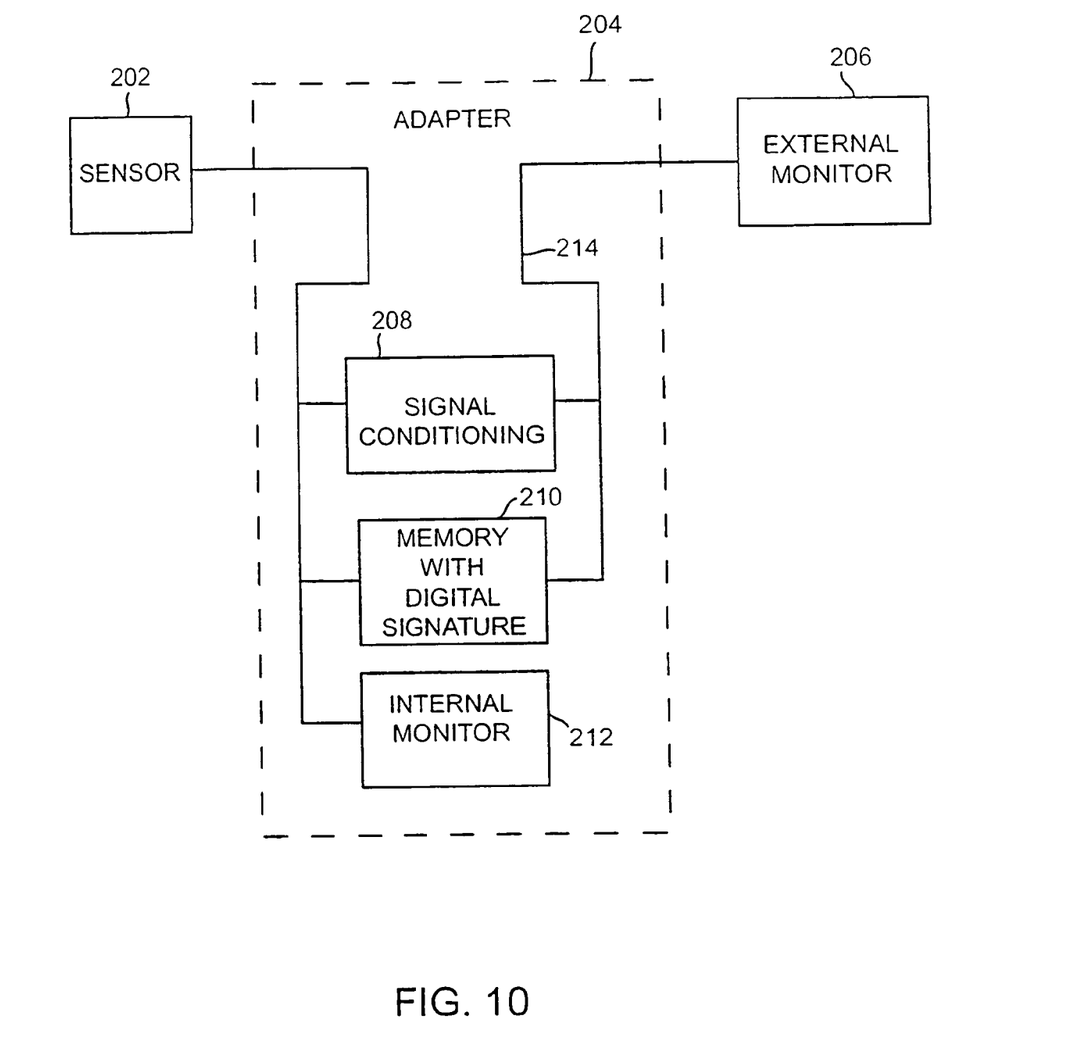
FIG. 10 is a block diagram of a sensor system using an adapter with a digital signature in the adapter.

FIG. 10 is a block diagram of a sensor system incorporating an adapter having a digital signature in the adapter. FIG. 10 shows a sensor 202 connected to an adapter 204, which in turn is connected to a monitor 206. The adapter includes signal conditioning circuitry 208, a memory with a digital signature 210, and an internal monitor 212. One use of such an adapter would be for a class of sensors designed to be connected to such an adapter without a digital signature. The adapter itself could provide the digital signature to the external monitor 206. Thus, for example, instead of each sensor being certified, a different method for determining that the sensors are certified can be used, with the adapter providing the certification to the external monitor.

In the embodiment shown in FIG. 10, the adapter also includes an internal monitor 212. This internal monitor can be used to provide output display or other signals which are different from, or variations of, the outputs and displays provided by external monitors 206 in the field. To ensure that any outputs or displays by the two monitors are consistent, signal conditioning block 208 can modify the sensor signal so that, in its modified form, the signal output on line 214 to external monitor 206 will cause external monitor 206 to create an output signal corresponding to that produced by internal monitor 212. For example, a patient signal can be obtained from sensor 202 corresponding to a pulse oximetry value. An estimation of saturation and heart rate can be generated on internal monitor 212, with block 208 generating a synthetic AC signal which it sends to external monitor 206. The construction of a synthetic signal would be such so as to ensure that the external monitor calculates a similar heart rate and saturation to internal monitor 212.

The digital signature can be a signature of any data including unfiltered patient data, filtered patient data, a synthetic patient physiological signal or any other data.

As will be understood by those of skill in the art, the present invention may be embodied in other specific forms without departing from the essential characteristics of the invention. Accordingly, the foregoing is intended to be illustrative, but not limiting, of the scope of the invention which is set forth in the following claims.

What is claimed is:

1. A pulse oximeter apparatus comprising:
a pulse oximeter sensor having an output for providing a signal corresponding to a measured physiological characteristic; and
a memory associated with the sensor and located external to a monitor configured to receive the sensor signal, the memory containing data relating to the sensor and containing a digital signature.

2. The apparatus of claim 1 wherein the digital signature is signed using a private key, the digital signature being verifiable with a public key in the monitor.

3. The apparatus of claim 1 wherein the digital signature comprises a Rabin-Williams signature, an RSA signature, a Diffie-Hellman signature, an El Gamal signature, or an elliptic curve signature.

4. The apparatus of claim 1 wherein at least a first portion of the data is contained within said digital signature.

5. The apparatus of claim 1 wherein the memory associated with the sensor is mounted in an adapter coupled between the sensor and the monitor.

6. A method for creating a digital signature in a pulse oximeter apparatus including a memory associated with a pulse oximeter sensor having an output configured to provide a signal corresponding to a measured physiological characteristic, the method comprising:
signing at least a portion of data relating to the sensor to create a digital signature;
storing the digital signature in the memory; and
storing data relating to the sensor in the memory.

7. The method of claim 6 comprising:
creating a public key and private key pair;
imbedding the public key in a memory in a sensor reader; and
using the private key to sign the data and create the digital signature.

8. The method of claim 6 wherein the digital signature comprises a Rabin-Williams signature, an RSA signature, a Diffie-Heilman signature, an El Gamal signature, or an elliptic curve signature.

9. The method of claim 6 comprising imbedding at least a portion of the data in the digital signature.

10. The method of claim 6 wherein the memory associated with the sensor is mounted in an adapter coupled between the sensor and a monitor.

11. A pulse oximeter sensor reader comprising:
a housing;
a sensor input for receiving a signal from a pulse oximeter sensor corresponding to a measured physiological characteristic;
a sensor processing circuit coupled to the sensor input;
a memory input for receiving digital data stored in a memory associated with the sensor, the digital data including a digital signature;
a first sensor reader memory coupled to the memory input for storing the digital data;
a second sensor reader memory storing a signature verification key;
a third sensor reader memory storing a program for verifying the digital signature of the digital data using the signature verification key; and
a transfer circuit for providing at least a portion of the digital data to the sensor processing circuit.

12. The sensor reader of claim 11 wherein the first and second sensor reader memories are different portions of the same physical memory.

13. The sensor reader of claim 11 wherein the sensor processing circuit comprises a microprocessor.

14. The sensor reader of claim 11 wherein the signature verification key is a public key of a private key and public key pair.

15. The sensor reader of claim 11 wherein the signature is a Rabin-Williams signature.

16. The sensor reader of claim 11 wherein at least a portion of the digital data is imbedded in the digital signature.

17. A pulse oximeter system comprising:
(a) a pulse oximeter sensor apparatus comprising
a sensor having an output configured to provide a signal corresponding to a measured physiological characteristic, and
a sensor memory associated with the sensor, the sensor memory having digital data relating to the sensor and having a digital signature, the digital signature being a signature of at least a portion of the data; and
(b) a pulse oximeter sensor reader comprising
a sensor reader housing;
a sensor input adapted to receive the signal from the sensor corresponding to the measured physiological characteristic;
a sensor processing circuit coupled to the sensor input;
a memory input adapted to receive the digital data from the sensor memory;
a first sensor reader memory coupled to the memory input to store the digital data;
a second sensor reader memory storing a signature verification key; and
a third sensor reader memory storing a program adapted to verify the digital signature using the signature verification key.

18. The system of claim 17 wherein the memory associated with the sensor is mounted in an adapter coupled between the sensor and the sensor reader.

19. A pulse oximeter apparatus comprising:
a sensor having an output configured to provide a sensor signal corresponding to a measured physiological characteristic; and
an adapter coupled to the sensor, the adapter including a memory, the memory containing sensor data and containing a digital signature.

20. The apparatus of claim 19 comprising:
an internal monitor in the adapter configured to provide an output signal corresponding to the physiological characteristic; and
a conditioning circuit configured to modify the sensor signal to produce a synthetic sensor signal, such that a second external monitor using the synthetic sensor signal produces an output corresponding to the output signal of the internal monitor.

* * * * *